United States Patent
Cartwright et al.

(12)

(10) Patent No.: US 6,552,223 B1
(45) Date of Patent: Apr. 22, 2003

(54) N-HYDROXACYLAMINO COMPOUNDS, PROCESS FOR THEIR PREPARATION AND PHARMACEUTICAL COMPOSITIONS CONTAINING THEM

(75) Inventors: Rebecca J Cartwright, Macclesfield (GB); Robert I Dowell, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/763,598

(22) PCT Filed: Aug. 25, 1999

(86) PCT No.: PCT/GB99/02809

§ 371 (c)(1),
(2), (4) Date: Feb. 26, 2001

(87) PCT Pub. No.: WO00/12467

PCT Pub. Date: Mar. 9, 2000

(30) Foreign Application Priority Data

Aug. 31, 1998 (EP) .............................................. 98402146

(51) Int. Cl.$^7$ ........................ C07C 259/04; A61K 31/19
(52) U.S. Cl. ........................ 562/621; 564/153; 514/575; 514/616
(58) Field of Search .................... 564/153; 514/616, 514/575; 562/621

(56) References Cited

FOREIGN PATENT DOCUMENTS

| EP | 0 082 088 | 6/1983 |
| WO | WO 92/09563 | 6/1992 |

*Primary Examiner*—Shailendra Kumar
(74) *Attorney, Agent, or Firm*—Ropes & Gray

(57) ABSTRACT

A compound of the formula (I):

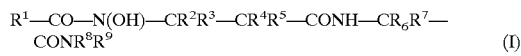

$R^1$—CO—N(OH)—$CR^2R^3$—$CR^4R^5$—CONH—$CR_6R^7$—$CONR^8R^9$ (I)

wherein:
  $R^1$ is $C_{1-6}$alkyl, aryl or aryl$C_{1-6}$alkyl;
  $R^2$ is hydrogen, $C_{1-6}$alkyl, $C_{3-8}$cycloalkyl, aryl or aryl$C_{1-6}$alkyl;
  $R^3$ is hydrogen, $C_{1-6}$alkyl or aryl$C_{1-6}$alkyl; or $R^2$ and $R^3$, together with the carbon atom to which they are joined, form a $C_{3-8}$cycloalkyl ring;
  $R^4$ is benzyl, phenethyl, phenylpropyl, phenylbutyl or flurophenylbutyl;
  $R^5$ is hydrogen, $C_{1-6}$alkyl or aryl$C_{1-6}$alkyl;
  $R^6$ is hydrogen, $C_{1-6}$alkyl, $C_{2-6}$alkenyl, $C_{3-8}$cycloalkyl$C_{1-6}$alkyl, aryl$C_{1-6}$alkyl, heteroaryl$C_{1-6}$alkyl or the side-chain of a naturally occurring amino acid;
  $R^7$ is hydrogen or $C_{1-6}$alkyl;
  $R^8$ is hydrogen, $C_{1-6}$alkyl, $C_{3-8}$cycloalkyl, $C_{3-8}$cycloalkenyl, aryl$C_{1-6}$alkyl, heteroaryl$C_{1-6}$alkyl or heterocyclyl$C_{1-6}$alkyl;
  $R^9$ is hydrogen or $C_{1-6}$alkyl;
  or $R^8$ and $R^9$, together with the nitrogen atom to which they are joined, form a heterocyclic ring;
  wherein any group or ring in $R^1$–$R^9$ is optionally substituted;
or a pharmaceutically-acceptable salt or in vivo hydrolysable precursor thereof.

7 Claims, No Drawings

N-HYDROXACYLAMINO COMPOUNDS, PROCESS FOR THEIR PREPARATION AND PHARMACEUTICAL COMPOSITIONS CONTAINING THEM

This application is the national phase of international application PCT/GB99/02809 filed Aug. 25, 1999 which designated the U.S.

This invention relates to (N-hydroxy)acylamino compounds and in particular to such compounds with a peptidic structure. This invention further relates to processes for preparing such compounds, to pharmaceutical and veterinary compositions containing them and to their use in methods of therapeutic treatment.

The compounds of this invention are inhibitors of one or more metalloproteinase enzymes. Metalloproteinases are a superfamily of proteinases (enzymes) whose numbers in recent years have increased dramatically. Based on structural and functional considerations these enzymes have been classified into families and subfamilies as described in N. M Hooper (1994) FEBS Letters 354:1–6. Examples of metalloproteinases include the matrix metalloproteinases (MMP) such as the collagenases (MMP1, MMP8, MMP13), the gelatinases (MMP2, MMP9), the stromelysins (MMP3, MMP10, MMP11), matrilysin (MMP7), metalloelastase (P12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265–279).

Metalloproteinases have been associated with many disease conditions. Inhibition of the activity of one or more metalloproteinases may well be of benefit in these disease conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease)); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; and extracellular matrix remodelling observed in cardiovascular diseases such as restenosis and atherosclerosis.

A number of metalloproteinase inhibitors are known; different classes of compounds may have different degrees of potency and selectivity for inhibiting various metalloproteinases. We have discovered a new class of compounds that are inhibitors of metalloproteinases and are of particular interest in inhibiting MMP-13. The compounds of this invention have beneficial potency and/or pharmacokinetic properties.

MMP13, or collagenase 3, was initially cloned from a cDNA library derived from a breast tumour [J. M. P. Freije et al. (1994) Journal of Biological Chemistry 269(24: 16766–16773]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., (1997) Cell Growth Differ. 8(2):243–250], squamous cell carcinomas [N. Johansson et al., (1997) Am. J. Pathol. 151(2):499–508] and epidermal tumours [K. Airola et al., (1997) J. Invest. Dermatol. 109(2):225–23 1]. These results are suggestive that MMP13 is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that MMP13 plays a role in the turnover of other connective tissues. For instance, consistent with MMP13's substrate specificity and preferential to degrade type II collagen [P. G. Mitchell et al., (1996) J. Clin Invest. 97(3):761–768; V. Knauper et al., (1996) The Biochemical Journal 271:1544–1550], MMP13 has been hypothesised to serve a role during primary ossification and skeletal remodelling [M. Stahle-Backdahl et al., (1997) Lab. Invest. 76(5):717–728; N. Johansson et al., (1997) Dev. Dyn. 208(3):387–397], in destructive joint diseases such as rheumatoid and osteo-arthritis [D. Wernicke et al., (1996) J. Rheumatol. 23:590–595; P. G. Mitchell et al., (1996) J. Clin. Invest. 97(3):761–768; O. Lindy et al., (1997) Arthritis Rheum 40(8):1391–1399]; and during the aseptic loosening of hip replacements [S. Imai et al., (1998) J. Bone Joint Surg. Br. 80(4):701–710]. MMP13 has also been implicated in chronic adult periodontitis as it has been localised to the epithelium of chronically inflamed mucosa human gingival tissue [V. J. Uitto et al., (1998) Am. J. Pathol 152(6):1489–1499] and in remodelling of the collagenous matrix in chronic wounds [M. Vaalamo et al., (1997) J. Invest. Dermatol. 109(1):96–101].

The present invention provides a compound of the formula (I):

$$R^1-CO-N(OH)-CR^2R^3-CR^4R^5-CONH-CR^6R^7-CONR^8R^9 \quad (I)$$

wherein:

$R^1$ is $C_{1-6}$alkyl, aryl or aryl$C_{1-6}$alkyl;

$R^2$ is hydrogen, $C_{1-6}$alkyl, $C_{3-8}$cycloalkyl, aryl or aryl$C_{1-6}$alkyl;

$R^3$ is hydrogen, $C_{1-6}$alkyl or aryl$C_{1-6}$alkyl;

or $R^2$ and $R^3$, together with the carbon atom to which they are joined, form a $C_{3-8}$cycloalkyl ring;

$R^4$ is hydrogen, $C_{1-6}$alkyl or aryl$C_{1-6}$alkyl;

$R^5$ is hydrogen, $C_{1-6}$alkyl or aryl$C_{1-6}$alkyl;

$R^6$ is hydrogen, $C_{1-6}$alkyl, $C_{2-6}$alkenyl, $C_{3-8}$cycloalkyl$C_{1-6}$alkyl, aryl$C_{1-6}$alkyl, heteroaryl$C_{1-6}$alkyl or the side-chain of a naturally occurring amino acid;

$R^7$ is hydrogen or $C_{1-6}$alkyl;

$R^8$ is hydrogen, $C_{1-6}$alkyl, $C_{3-8}$cycloalkyl, $C_{3-8}$cycloalkenyl, aryl$C_{1-6}$alkyl, heteroaryl$C_{1-6}$alkyl or heterocyclyl$C_{1-6}$alkyl;

$R^9$ is hydrogen or $C_{1-6}$alkyl;

or $R^8$ and $R^9$, together with the nitrogen atom to which they are joined, form a heterocyclic ring;

wherein any group or ring in $R^1$–$R^9$ is optionally substituted;

or a pharmaceutically-acceptable salt or in vivo hydrolysable precursor thereof

"Aryl" in the terms "aryl" and "aryl$C_{1-6}$alkyl" typically means phenyl or naphthyl, preferably phenyl. "Heteroaryl" in the terms "heteroaryl" and "heteroaryl$C_{1-6}$alkyl" means an aromatic mono- or bicyclic 5–10 membered ring with up to five ring heteroatoms selected from nitrogen, oxygen and sulphur. Examples of 'heteroaryl' include thienyl, pyrrolyl, furanyl, imidazolyl, thiazolyl, pyrimidinyl, pyridinyl, indolyl, benzimidazolyl, benzthiazolyl, quinolinyl and isoquinolinyl. "Heterocyclyl" in the terms "heterocyclyl" and heterocyclyl$C_{1-6}$alkyl" means a non-aromatic mono- or bicyclic 5–10 membered ring with up to five ring hetero atoms selected from nitrogen, oxygen and sulphur. Examples of 'heterocyclyl' include pyrrolidinyl, morpholinyl, piperidinyl, dihydropyridinyl and dihydropyrimidinyl.

Any group or ring in $R^1$–$R^9$ may be optionally substituted, for example by up to three substituents which may be the same or different. Typical substituents include: hydroxy, $C_{1-6}$alkoxy for example methoxy, mercapto, $C_{1-6}$alkylthio for example methylthio, amino, $C_{1-6}$alalkylamino for example methylamino, di-($C_{1-6}$alkyl)amino for example dimethylamino, carboxy, carbamoyl, $C_{1-6}$alkylcarbamoyl for example methylcarbamoyl, di-$C_{1-6}$alkylcarbamoyl for example dimethylcarbamoyl, $C_{1-6}$alkylsulphonyl for example methylsulphonyl, arylsulphonyl for example phenylsulphonyl, $C_{1-6}$alkylaminosulphonyl for example methylaminosulphonyl, di-($C_{1-6}$alkyl)aminosulphonyl for example dimethylamino-sulphonyl, nitro, cyano, cyano$C_{1-6}$alkyl for example cyanomethyl, hydroxy$C_{1-6}$alkyl for example hydroxymethyl, amino$C_{1-6}$alkyl for example aminoethyl, $C_{1-6}$alkanoylamino for example acetamido, $C_{1-6}$alkoxycarbonylamino for example methoxycarbonylamino, $C_{1-6}$alkanoyl for example acetyl, $C_{1-6}$alkanoyloxy for example acetoxy, $C_{1-6}$alalkyl for example methyl, ethyl, isopropyl or tert-butyl, halo for example fluoro, chloro or bromo, trifluoromethyl, aryl for example phenyl, aryl$C_{1-6}$alkyl for example benzyl, aryloxy for example phenoxy, aryl$C_{1-6}$alkoxy for example benzyloxy, heteroaryl, heteroaryl$C_{1-6}$alkyl, heterocyclyl and heterocyclyl$C_{1-6}$alkyl. The term "side chain of a naturally occurring amino acid" means the side chain X of an amino acid $NH_2$—CHX—COOH. Suitable amino acids include alanine, arginine, aspartic acid, cysteine, asparagine, glutamine, histidine, homoserine, isoleucine, leucine, lysine, methionine, norleucine, norvaline, ornithine, serine, threonine, tryptophan, tyrosine and valine.

The compounds of the present invention possess a number of chiral centres (dependent on the nature of the variable), for example at —$CR^2R^3$—, at —$CR^4R^5$—, at —$CR^6R^7$— and possibly in the variables $R^1$–$R^9$. The present invention covers all isomers, diastereoisomers, etc. and mixtures thereof that inhibit one or more metalloproteinase enzymes.

Particular groups for $R^1$ include $C_{1-6}$alkyl for example methyl, ethyl, isopropyl, n-propyl, isobutyl, sec-butyl, n-butyl, tert-butyl, isopentyl, n-pentyl or hexyl; $C_{1-6}$alkyl interrupted by an oxygen or sulphur atom for example methoxymethyl, methoxyethyl, ethoxyethyl, methoxyethyl, methoxypropyl, ethoxyethyl, propoxymethyl, ethylthioethyl or methylthiopropyl; phenyl$C_{1-6}$alkyl for example benzyl, phenethyl, phenylpropyl or phenylbutyl; phenyl$C_{1-6}$alkyl interrupted by oxygen or sulphur for example benzyloxybutyl or benzyloxypropyl; and aryl for example phenyl or trifluoromethylphenyl.

Preferably $R^1$ is methyl, ethyl, isopropyl, tert-butyl, isobutyl, benzyl, phenethyl or phenyl.

Particular groups for $R^2$ include hydrogen, $C_{1-6}$alkyl for example methyl or ethyl; $C_{3-8}$cycloalkyl for example cyclobutyl, cyclopentyl or cyclohexyl; aryl for example phenyl; and aryl$C_{1-6}$alkyl for example benzyl, phenethyl or phenylpropyl.

Preferably $R^2$ is hydrogen or methyl.

Particular groups for $R^3$ include hydrogen; $C_{1-6}$alkyl for example methyl or ethyl; and aryl$C_{1-6}$alkyl for example benzyl or phenethyl.

Preferably $R^3$ is hydrogen.

Particular groups for $R^4$ include hydrogen; $C_{1-6}$alkyl for example methyl, ethyl, isopropyl, n-propyl, isobutyl, sec-butyl, n-butyl, tert-butyl, isopentyl, n-pentyl or hexyl; $C_{1-6}$alkyl interrupted by an oxygen or sulphur atom for example methoxymethyl, methoxyethyl, ethoxyethyl, methoxyethyl, methoxypropyl, ethoxyethyl, propoxymethyl, ethylthioethyl or methylthiopropyl; phenyl$C_{1-6}$alkyl for example benzyl, phenethyl, phenylpropyl or phenylbutyl; halophenyl$C_{1-6}$alkyl for example fluorophenethyl, fluorophenylpropyl, fluorophenylbutyl or chlorophenylbutyl; and phenyl$C_{1-6}$alkyl interrupted by oxygen or sulphur for example benzyloxybutyl or benzyloxypropyl.

Preferably $R^4$ is benzyl, phenethyl, phenylpropyl, phenylbutyl or fluorophenylbutyl.

Particular groups for $R^5$ include hydrogen; $C_{1-6}$alkyl for example methyl or ethyl; and phenyl$C_{1-6}$alkyl for example benzyl.

Preferably $R^5$ is hydrogen or methyl.

There is a chiral centre at —$CR^4R^5$— (when $R^4$ and $R^5$ are not the same); it is preferred that this centre has the configuration indicated in formula (II) hereinafter. For example, for most values of $R^4$ (when $R^5$ is hydrogen), this centre will have the R stereochemistry under the Cahn-Prelog-Ingold sequence rules.

Particular groups for $R^6$ include $C_{1-6}$alkyl for example methyl, ethyl, isopropyl, n-propyl, n-butyl, isobutyl, sec-butyl, tert-butyl, isopentyl, n-pentyl or hexyl; $C_{1-6}$alkyl interrupted by an oxygen or sulphur atom for example methoxyethyl, methoxypropyl, methylthioethyl or 1,1-dimethylmethylthiomethyl ($MeSCMe_2$—); $C_{3-8}$cycloalkyl$C_{1-6}$alkyl for example cyclopentylmethyl, cyclohexylmethyl or cycloheptylmethyl; or phenyl$C_{1-6}$alkyl for example benzyl or phenethyl.

Preferably $R^6$ is isobutyl, tert-butyl, 1,1-dimethylmethylthiomethyl, cyclopentylmethyl, cyclohexylmethyl or benzyl with tert-butyl being most preferred.

Particular groups for $R^7$ include hydrogen or $C_{1-6}$alkyl for example methyl or ethyl.

Preferably $R^7$ is hydrogen.

There is a chiral centre at —$CR^6R^7$— (when $R^6$ and $R^7$ are not the same); it is preferred that this centre has the configuration indicated in formula (II) hereinafter. For example, for most values of $R^6$ (when $R^7$ is hydrogen) this centre will have the S-stereochemistry.

Particular groups for $R^8$ include $C_{1-6}$alkyl for example methyl, ethyl, n-propyl, isopropyl, tert-butyl or n-butyl; $C_{1-6}$alkyl interrupted by an oxygen or sulphur atom for example hydroxyethyl, methoxyethyl, methylthioethyl or ethoxyethyl; $C_{2-6}$alkyl substituted by either amino, $C_{1-6}$alkylamino or di-$C_{1-6}$alkylamino; phenyl$C_{1-6}$alkyl for example benzyl, phenethyl or phenylpropyl; heterocyclicalkyl for example 2-morpholinoethyl, 2-piperazinoethyl, 2-(N-methylpiperazino)ethyl or 2-piperidinoethyl; or $C_{3-8}$cycloalkyl$C_{1-6}$alkyl for example cyclopropylmethyl cyclobutylmethyl or cyclopentylmethyl.

Preferably $R^8$ is methyl, ethyl, n-propyl, isobutyl tert-butyl, benzyl or phenethyl. Of these methyl is most preferred.

Particular groups for $R^9$ are hydrogen and $C_{1-6}$alkyl for example methyl or ethyl. Preferably $R^9$ is hydrogen.

A particularly suitable class of compounds of the present invention is that of formula (II):

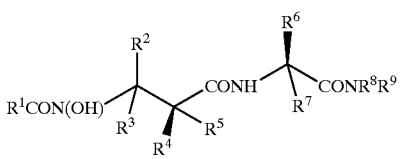
(II)

wherein $R^1$–$R^9$ are as hereinbefore defined.

A preferred class of compounds of the formula (II) is that wherein $R^1$ is methyl, ethyl, isopropyl, benzyl, phenethyl or phenyl, $R^2$, $R^3$, $R^5$ and $R^7$ are all hydrogen; $R^4$ is benzyl, phenethyl, phenylpropyl, phenylbutyl or 4-fluorophenylbutyl; $R^6$ is isobutyl, tert-butyl, 1,1-dimethylmethylthiomethyl, cyclopentylmethyl, cyclohexylmethyl or benzyl; $R^8$ is methyl, ethyl, n-propyl, isobutyl, tert-butyl, 2-dimethylaminoethyl, benzyl or phenethyl, and $R^4$ is hydrogen or methyl.

Particular compounds of this invention include those of the examples hereinbelow and those of the formula (II) wherein $R^1$ is phenyl or tert-butyl; $R^4$ is phenylpropyl; $R^6$ is tert-butyl; $R^8$ is methyl and $R^2$, $R^3$, $R^5$ and $R^7$ are each hydrogen.

Suitable pharmaceutically acceptable salts include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

In vivo hydrolysable precursors are those pharmaceutically acceptable precursors that hydrolyse in the human body to produce the parent compound. Such precursors can be identified by administering, for example intravenously to a test animal, the compound under test and subsequently examining the test animal's body fluids. Suitable in vivo hydrolysable precursors include esters, suitable examples of which for carboxy include methoxymethyl and for hydroxy include acetyl.

In order to use a compound of the formula (I) or a pharmaceutically acceptable salt or in vivo hydrolysable precursor thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in vivo hydrolysable precursor and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formula (I) or a pharmaceutically acceptable salt or in vivo hydrolysable precursor thereof for use in a method of therapeutic treatment of the human or animal body.

In yet a further aspect the present invention provides a method of treating a disease condition mediated by one or more metalloproteinase enzymes which comprises administering to a warm-blooded animal an effective amount of a compound of the formula (I) or a pharmaceutically acceptable salt or in vivo hydrolysable precursor thereof. The present invention also provides the use of a compound of the formula (I) or a pharmaceutically acceptable salt or in vivo hydrolysable precursor thereof in the preparation of a medicament for use in a disease condition mediated by one or more metalloproteinase enzymes.

In another aspect the present invention provides a process for preparing a compound of the formula (I) or a pharmaceutically acceptable salt or in vivo hydrolysable precursor thereof which process comprises deprotecting a compound of the formula (III):

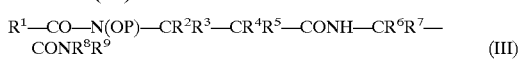
(III)

wherein $R^1$–$R^9$ as defined hereinbefore and P is a protecting group:
wherein any other functional group is protected, if necessary, and:
  i) removing any other protecting groups;
  ii) optionally forming a pharmaceutically acceptable salt or in vivo hydrolysable precursor.

P is any suitable protecting group known for protecting the O-atom of a hydroxylamine group. Typically P is benzyl, substituted benzyl such as p-methoxybenzyl, tert-butyl or silyl. Such groups may be removed under standard conditions known in the art; for example a benzyl protecting group may be removed by catalytic hydrogenation.

Protecting groups may in general be chosen from any of the groups described in the literature or known to the skilled chemist as appropriate for the protection of the group in question, and may be introduced by conventional methods; see for example Protecting Groups in Organic Chemistry; Theodora W. Greene.

Protecting groups for other functional groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the salke of convenience. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing $C_{1-20}$ carbon atoms).

Examples of carboxy protecting groups include straight or branched chain $C_{1-12}$ alkyl groups (eg isopropyl, t-butyl); $C_{1-4}$ alkoxy$C_{1-4}$ alkyl groups (eg methoxymethyl, ethoxymethyl, isobutoxymethyl); $C_{1-4}$ acyloxy$C_{1-4}$ alkyl groups, (eg acetoxymethyl, propionyloxymethyl, butyryloxymethyl, pivaloyloxymethyl), $C_{1-4}$ alkoxycarbonyloxy $C_{1-4}$ alkyl groups (eg 1-methoxycarbonyloxyethyl, 1-ethoxycarbonyloxyethyl); aryl $C_{1-4}$ alkyl groups (eg benzyl, p-methoxybenzyl, o-nitrobenzyl, p-nitrobenzyl, benzhydryl and phthalidyl); tri($C_{1-4}$ alkyl)silyl groups (eg trimethylsilyl and t-butyldimethylsilyl); tri($C_{1-4}$ alkyl)silyl lower alkyl groups (eg trimethylsilylethyl); and $C_{2-6}$ alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include $C_{1-4}$ alkyl groups (eg t-butyl), $C_{2-4}$ alkenyl groups (eg allyl); $C_{1-4}$ alkanoyl groups (eg acetyl); $C_{1-4}$ alkoxycarbonyl groups (eg t-butoxycarbonyl); $C_{2-4}$ alkenyloxycarbonyl groups (eg allyloxycarbonyl); aryl$C_{1-4}$ alkoxycarbonyl groups (eg benzoyloxycarbonyl, p-methoxybenzyloxycarbonyl, o-nitrobenzyloxycarbonyl, p-nitrobenzyloxycarbonyl); tri-$C_{1-4}$ alkylsilyl (eg trimethylsilyl, t-butyldimethylsilyl) and aryl$C_{1-4}$ alkyl (eg benzyl) groups.

Examples of amino protecting groups include formyl, aralkyl groups (eg benzyl and substituted benzyl, p-methoxybenzyl, nitrobenzyl and 2,4-dimethoxybenzyl, and triphenylmethyl); di-p-anisylmethyl and furylmethyl groups; $C_{1-4}$ alkoxycarbonyl (eg t-butoxycarbonyl); $C_{2-4}$ alkenyloxycarbonyl (eg allyloxycarbonyl); aryl $C_{1-4}$ alkoxycarbonyl groups (eg benzyloxycarbonyl, p-methoxybenzyloxycarbonyl, o-nitrobenzyloxycarbonyl, p-nitrobenzyloxycarbonyl); tri$C_{1-4}$ alkylsilyl (eg trimethylsilyl and t-butyldimethylsilyl); alkylidene (eg methylidene); benzylidene and substituted benzyldene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The compounds of the formula (III) may be prepared by:
a) reacting a compound of the formula (IV) with a compound of the formula (V):

$$R^1—CO—N(OP)—CR^2R^3—CR^4R^5—COOH \quad (IV)$$

$$NH_2—CR^6R^7—CONR^8R^9 \quad (V)$$

wherein $R^1$–$R^9$ and P are as hereinbefore defined, under standard peptide coupling conditions;

b) reacting a compound of the formula (VI) with a compound of the formula (VII):

$$R^1—CO—N(OP)—CR^2R^3—CR^4R^5—CONH—CR^6R^7—COOH \quad (VI)$$

$$HNR^8R^9 \quad (VII)$$

wherein $R^1$–$R^9$ and P are as hereinbefore defined, under standard peptide coupling conditions;

c) acylating a compound of the formula (VIII) with an acylating agent $R^1$—CO—X:

$$P^1O—HN—CR^2R^3—CR^4R^5—CONH—CR^6R^7—CONR^8R^9 \quad (VIII)$$

wherein $R^1$–$R^9$ are as hereinbefore defined and $P^1$ is hydrogen or a group P as hereinbefore defined.

Standard peptide coupling conditions are described in many articles and textbooks.

The compounds of the formula (V) may be prepared by reacting a compound of the formula (VII) with a compound of the formula (IX) under standard peptide coupling conditions:

$$NH_2CR^6R^7COOH \quad (IX)$$

wherein $R^6$ and $R^7$ are as hereinbefore defined.

The compounds of the formula (IV) may be prepared by standard methods of organic synthesis, for example see the methods of the Examples hereinbelow.

The compounds of the formula (VI) may be prepared by reacting a compound of the formula (IV) with a compound of the formula (IX) under standard peptide coupling conditions.

The compounds of the formula (VIII) are acylated to form the compounds of the formula (III). When $P^1$ is hydrogen, acylation may result in acylation on both the nitrogen and oxygen atoms of the hydroxylamine function. If this is the case, the O-acyl group may be removed under standard deprotection conditions.

Suitable acylating agents include acetyl chloride, acetic anhydride and related compounds.

The compounds of the formula (VIII) are prepared by methods similar to those described hereinabove for preparing the compounds of the formula (III).

The following biological test methods and Examples serve to illustrate the invention.

ISOLATED ENZYME ASSAYS

Matrix Metalloproteinase Family Including for Example MMP13

Recombinant human proMMP13 may be expressed and purified as described by Knauper et al. [V. Knauper et al., (1996) The Biochemical Journal 271:1544–1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4–5 hours at 35° C. in assay buffer (0.1M Tris-HCl, pH 7.5 containing 0.1M NaCl, 20 mM $CaCl_2$, 0.02 mM ZnCl and 0.05% (w/v) Brij 35 using the synthetic substrate 7-methoxycoumarin-4-yl)acetyl.Pro.Leu.Gly.Leu.N-3-(2,4- dinitrophenyl)-L-2,3diaminopropionyl.Ala.Arg.NH$_2$ in the presence or absence of inhibitors. Activity is determined by measuring the fluorescence at λex 328 nm and λem 393 nm. Percent inhibition is calculated as follows: % Inhibition is equal to the

[Fluorescence$_{plus\ inhibitor}$–Fluorescence$_{background}$] divided by the [Fluorescence$_{minus\ inhibitor}$–Fluorescence$_{background}$].

A similar protocol can be used for other expressed and purified pro MMPs using substrates and buffers conditions optimal for the particular MMP, for instance as described in C. Graham Knight et al., (1992) FEBS Lett. 296(3): 263–266.

Adamalysin Family Including for Example TNF Convertase

The ability of the compounds to inhibit proTNFα convertase enzyme may be assessed using a partially purified, isolated enzyme assay, the enzyme being obtained from the membranes of THP-1 as described by K. M. Mohler et al., (1994) Nature 370:218–220. The purified enzyme activity and inhibition thereof is determined by incubating the partially purified enzyme in the presence or absence of test compounds using the substrate 4',5'-Dimethoxyfluoresceinyl Ser.Pro.Leu.Ala.Gln.Ala. Val.Arg. Ser. Ser. Ser. Arg.Cys(4-(3-succinimid-1-yl)-fluorescein)-NH$_2$ in assay buffer (50 mM Tris HCl, pH 7.4 containing 0.1% (w/v) Triton X-100 and 2 mM CaCl$_2$), at 26° C. for 18 hours. The amount of inhibition is determined as for MMP13 except λex 490 nm and λem 530 nm were used. The substrate was synthesised as follows. The peptidic part of the substrate was assembled on Fmoc-NH-Rink-MBHA-polystyrene resin either manually or on an automated peptide synthesiser by standard methods involving the use of Fmoc-amino acids and O-benzotriazol-1-yl-N,N,N',N'-tetramethyluronium hexafluorophosphate (HBTU) as coupling agent with at least a 4- or 5-fold excess of Fmoc-amino acid and HBTU. Ser$^1$ and Pro$^2$ were doublecoupled. The following side chain protection strategy was employed; Ser$^1$(Bu$^t$), Gln$^5$(Trityl), Arg$^{8,12}$(Pmc or Pbf), Ser$^{9,10,11}$(Trityl), Cys$^{13}$(Trityl). Following assembly, the N-terminal Fmoc-protecting group was removed by treating the Fmoc-peptidyl-resin with in DMF. The amino-peptidyl-resin so obtained was acylated by treatment for 1.5–2 hr at 70° C. with 1.5–2 equivalents of 4',5'-dimethoxy-fluorescein-4(5)coxylic acid [Khanna & Ullman, (1980) Anal Biochem. 108:156–161) which had been preactivated with diisopropylcarbodiimide and 1-hydroxybenzotriazole in DMF]. The dimethoxyfluoresceinyl-peptide was then simultaneously deprotected and cleaved from she resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-(N-maleimido)-fluorescein in DMF containing diisopropylethylamine, the product purified by RP-HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosure of E. C. Arner et al., (1998) Osteoarthritis and Cartilage 6:214–228 and the antibodies described therein. The potency of compounds to act as inhibitors against collagenases can be determined as described by T. Cawston and A. Barrett (1979) Anal. Biochem. 99:340–345.

INHIBITION OF METALLOPROTEINASE ACTIVITY IN CELL/TISSUE BASED ACTIVITY

Test as an Agent to Inhibit Membrane Sheddases Such as TNF Convertase

The ability of the compounds of this invention to inhibit the cellular processing of TNFα production may be assessed in THP-1 cells using an ELISA to detect released TNF essentially as described K. M. Mohler et al., (1994) Nature 370:218–220. In a similar fashion the processing or shedding of other membrane molecules such as those described in N. M. Hooper et al., (1997) Biochem. J. 321:265–279 may be tested using appropriate cell lines and with suitable antibodies to detect the shed protein.

Test as an Agent to Inhibit Cell Based Invasion

The ability of the compound of this invention to inhibit the migration of cells in an invasion assay may be determined as described in K Albini et al., (1987) Cancer Research 47:3239–3245.

Test as an Agent to Inhibit Whole Blood TNF Sheddase Activity

The ability of the compounds of this invention to inhibit TNFα production is assessed in a human whole blood assay where LPS is sed to stimulate the release of TNFα. Heparinized (10 Units/ml) human blood obtained from volunteers is diluted 1:5 with medium (RPMI1640+bicarbonate, penicillin, streptomycin and glutamine) and incubated (160 μl) with 20 μl of test compound (triplicates), in DMSO or appropriate vehicle, for 30 min at 37° C. in a humidified (5% CO$_2$/95% air) incubator, prior to addition of 20 μl LPS (E. coli. 0111:B4; final concentration 10 μg/ml). Each assay includes controls of diluted blood incubated with medium alone (6 wells/plate) or a known TNFα inhibitor as standard. The plates are then incubated for 6 hours at 37° C. (humidified incubator), centrifuged (200 rpm for 10 min; 4° C.), plasma harvested (50–100 μl) and stored in 96 well plates at −70° C. before subsequent analysis for TNFα concentration by ELISA.

Test as an Agent to Inhibit in Vitro Cartilage Degradation

The ability of the compounds of this invention to inhibit the degradation of the aggrecan or collagen components of cartilage can be assessed essentially as described by K. M. Bottomley et al., (1997) Biochem J. 323:483–488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e.g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are talken from an appropriate vessel into 10U heparin. Plasma fractions are obtained following centrifugation and the plasma proteins precipitated with acetonitrile (80% w/v final concentration). After 30 mins at −20° C. the plasma proteins are sedimented by centrifugation and the supernatant fraction is evaporated to dryness using a Savant speed vac. The sediment is reconstituted in assay buffer and subsequently analysed for compound content using the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve talking into account the total plasma dilution factor.

IN VIVO ASSESSMENT

Test as an Anti-TNF Agent

The ability of the compounds of this invention as ex vivo TNFα inhibitors is assessed in the rat. Briefly, groups of male Wistar Alderley Park (AP) rats (180–210 g) are dosed with compound (6 rats) or drug vehicle (10 rats) by the appropriate route e.g. peroral (p.o.), intraperitoneal (i.p.), subcutaneous (s.c.). Ninety minutes later rats are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 μl of each sample are added to a set format pattern in a 96U well plate. Fifty μl of heparinized human blood is then added to each well, mixed and the plate is incubated for 30 min at 37° C. (humidified incubator). LPS (25 μl; final concentration 10 μg/ml) is added to the wells and incubation continued for a further 5.5 hours. Control wells are incubated with 25 μl of medium alone. Plates are then centrifuged for 10 min at 2000 rpm and 200 μl of the supernatants are transferred to a 96 well plate and frozen at −20° C. for subsequent analysis of TNF concentration by ELISA. Data analysis by dedicated software calculates for each compound/dose:

Percent inhibition of TNFα=Mean TNFα (Controls)−Mean TNFα (Treated)×100 Mean TNFα (Controls)

Test as an Anti-arthritic Agent

Activity of a compound as an anti-arthritic is tested in the collagen-induced arthritis (CIA) as defined by D. E. Trentham et al., (1977) J. Exp. Med. 146,:857. In this model acid soluble native type II collagen causes polyarthritis in rats when administered in Freunds incomplete adjuvant. Similar conditions can be used to induce arthritis in mice and primates.

Test as an Anti-cancer Agent

Activity of a compound as an anti-cancer agent may be assessed essentially as described in I. J. Fidler (1978) Methods in Cancer Research 15:399439, using for example the B16 cell line (described in B. Hibner et al., Abstract 283 p75 10th NCI-EORTC Symposium Amsterdam Jun. 16–19, 1998).

In the examples:
(a) NMR spectra were talken at 300 MHz;
(b) Evaporation of solvents was carried out under reduced pressure after drying over anhydrous magnesium sulphate,
(c) DMSO means dimethylsulphoxide;
(d) Unless stated otherwise all chromatography was done on Merck 9385 silica using the flash technique.

EXAMPLES

Example 1

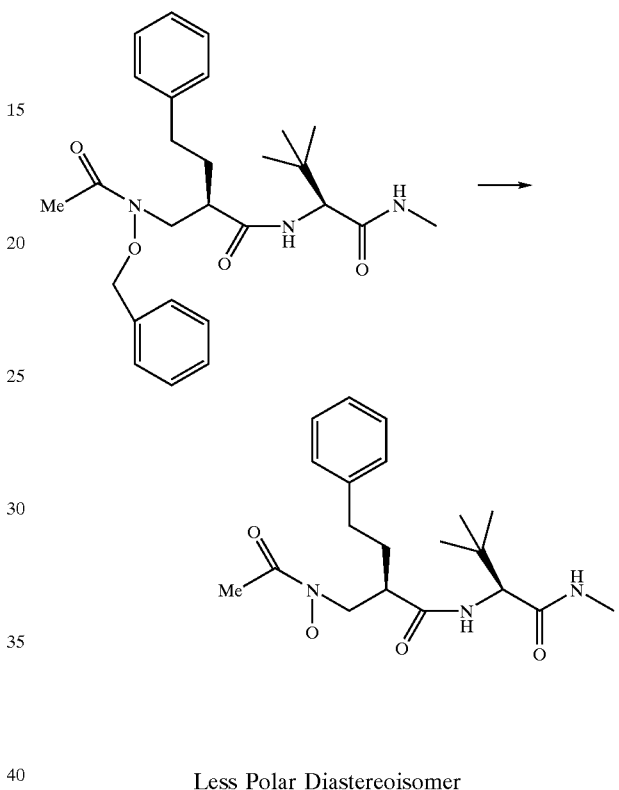

Less Polar Diastereoisomer

The less polar diastereoisomer (560 mg) was dissolved in ethanol (50 mL) and 10% palladium on carbon (100 mg) was added. The mixture was stirred under an atmosphere of hydrogen for 8 hours. The catalyst was removed by filtration though diatomaceous earth and the filtrate was evaporated to give the depicted product as an oil (233 mg): NMR DMSOd$_6$ δ 7.9 (d, 1H); 7.6 (d, 1H); 7.3–7.1 (m, 5H); 4.2 (d, 1H); 3.6 (m, 2H); 2.4 (m, 4H); 1.9 (s, 3H); 1.6 (m, 4H); 0.8 (s, 9H).

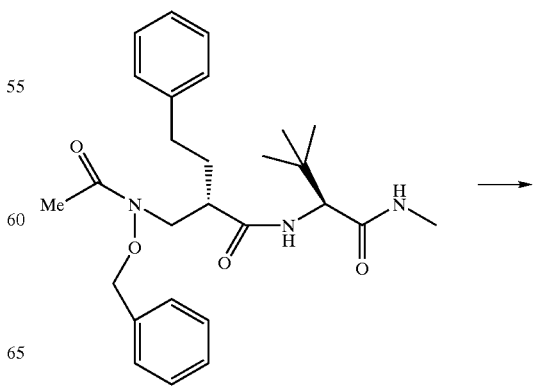

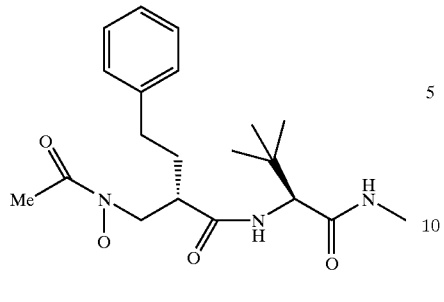

The more polar diastereoisomer (680 mg) was hydrogenated as above to give the depicted product as an oil (270 mg): NMR DMSOd$_6$ δ 7.9 (d, 1H); 7.8 (d, 1H); 7.3–7.1 (m, 5H); 4.2 (d, 1H); 3.6 (m, 2H); 2.4 (m, 4H); 1.9 (s, 3H); 1.6 (m, 4H); 0.95 (s, 9H).

The diastereoisomeric starting materials for these reactions were prepared as follows:

Step A

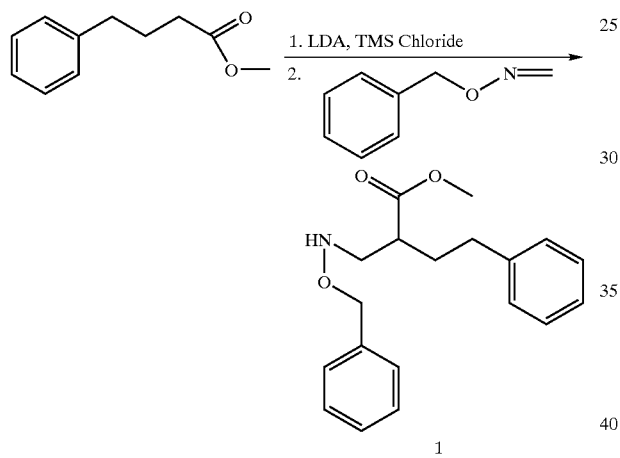

To a 2.0 M solution of lithium diisopropylamide (86.3 mL, 0.173M) cooled to −70° C., under an inert atmosphere, was added methyl 4-phenylbutenoate[1] (20.5 g, 0.115M). The addition was performed slowly to keep the temperature at −70° C. The mixture was stirred at −70° C. for 30 mins, chlorotrimethylsilane (34.5 mL, 0.369M) was added and the mixture was stirred for a further 90 minutes at −70° C. and then allowed to warm to ambient temperature for 18 hours. The mixture was evaporated to dryness, and the residue treated with isohexane. The insoluble material was removed by filtration and the filtrate was evaporated to dryness to give a residue. This oily residue (27.3 g, 0.109M) was dissolved in dichloromethane (400 mL) and O-benzyl formaldoxime[2] (14.7 g 0.109M) was added. The mixture was cooled to −10° C., under argon, and trimethylsilyl triflate (2.1 mL, 0.0109M) was added dropwise with stirring to maintain the temperature at −10° C. for 10 minutes. The mixture was stirred for 18 hours at ambient temperature, washed with sodium bicarbonate solution, washed with brine, dried and evaporated to dryness. The residue was subjected to chromatography and elution with ethyl acetate/hexane (1:9) gave 1 (10.3 g) as an oil: NMR CDCl$_3$ δ 7.4–7.1 (m, 10H); 5.7 (s, 1H); 4.6 (s, 2H); 3.6 (s, 3H); 3.2 (m, 1H); 3.1 (m, 1H); 2.8 (m, 1H); 2.6 (m, 2H); 2.0–1.8 (m, 2H).

Step B

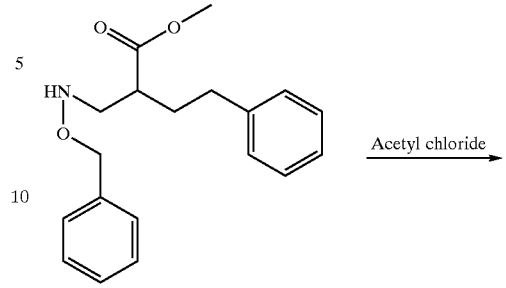

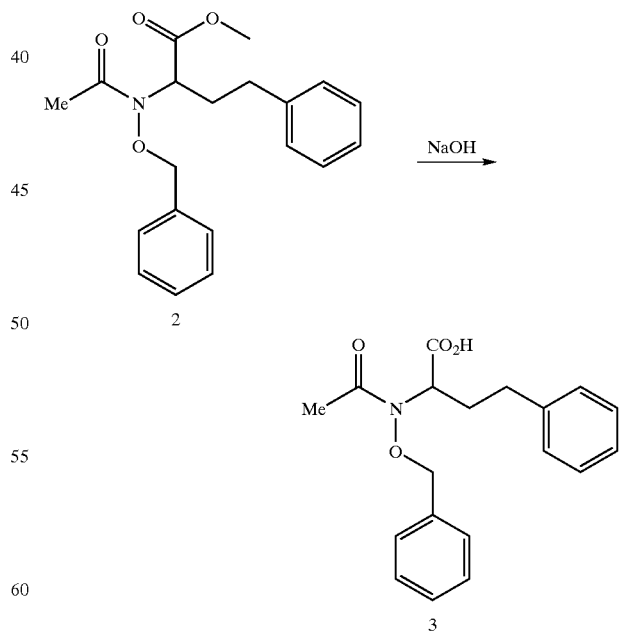

To the ester 1 (3.13 g 10 mM) in dichloromethane (50 mL) and triethylamine (2.9 mL, 20 mM) at 0° C. was slowly added acetyl chloride (0.71 mL; 10 mM). The mixture was then stirred for 18 hours at ambient temperature, washed with sodium bicarbonate solution, dried and evaporated to dryness. The residue was subjected to chromatography and elution with ethyl acetate/hexane (1:2) gave 2 as an oil (2.8 g; 7.6 mM): NMR CDCl$_3$ δ 7.4–7.1 (m, 10H); 4.8 (q, 2H); 3.9 (d, 1H); 3.8 (m, 1H); 3.6 (s, 3H); 2.8 (m, 1H); 2.6 (m, 2H); 2.1 (s, 3H); 2.0–1.8 (m, 2H).

Step C

This oil was dissolved in methanol (100 mL), sodium hydroxide (0.46 g, 11.4 mM) in water (10 mL) was added and the mixture was stirred for 18 hours at ambient temperature. After evaporation to dryness the residue was dissolved in water and extracted with ethyl acetate. The aqueous phase was acidified with 2M HCl and re-extracted twice with ethyl acetate. The combined organic extracts were dried and evaporated to dryness to give the acid 3 (1.6 g) which was used without further purification: NMR CDCl$_3$ δ 7.3–7.1 (m, 10H); 4.8 (q, 2H); 3.95 (d, 2H); 2.8 (m, 1H); 2.7 (m, 2H); 1.9 (s, 3H); 1.9–1.7 (m, 2H).

Step D

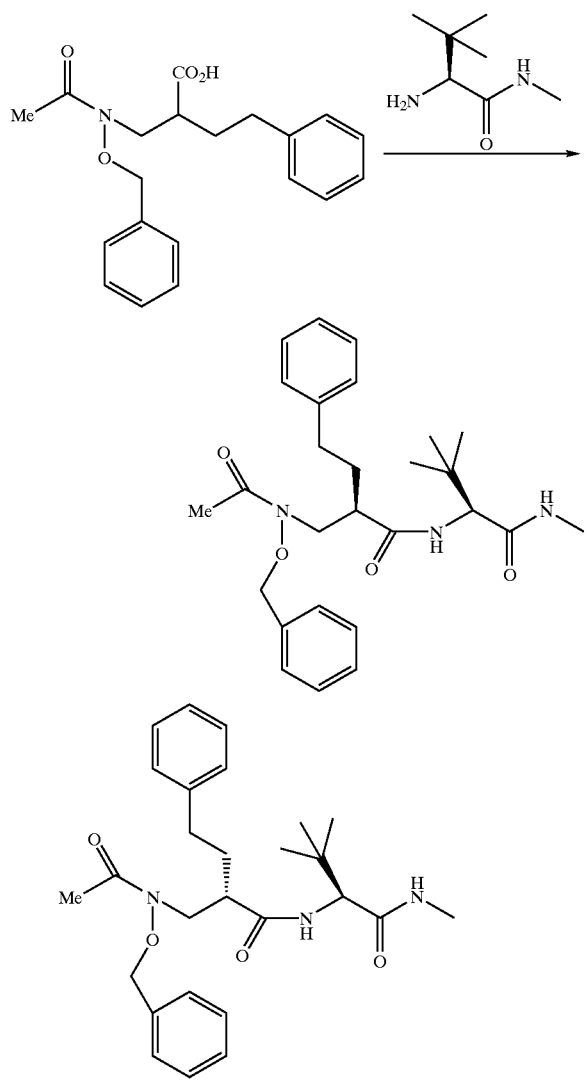

To the acid 3 (1.6 g, 4.7 mM) in dichloromethane (50 mL) was added 1-hydroxybenztriazole (650 mg, 4.7 mM), triethylamine (0.85 mL; 6 mM), S-tertbutyl-leucine N methyl amide (677 mg, 4.7 mM) and 1-(3-dimethylaminopropyl)-3-ethyl carbodiimide hydrochloride (1.16 g; 6 mM). The mixture was stirred for 18 hours at ambient temperature, washed with 1M citric acid, water, sodium bicarbonate solution, dried, and evaporated to dryness. The residue was subjected to chromatography on Kromasil C60 10 micron silica gel and elution with ethyl acetate/dichloromethane (40/60) gave the two separate diastereoisomers as oils; the less polar isomer (584 mg) and the more polar isomer (704 mg):

Less polar isomer NMR CDCl$_3$ δ 7.4–7.1 (m, 10H); 6.3 (d, 1H); 6.1 (d, 1H); 4.7 (s, 2H); 4.2 (d, 1H); 3.9 (m, 2H); 2.8 (d, 3H); 2.6 (m, 3H); 2.1 (s, 3H); 1.8 (m, 2H); 0.9 (s, 9H).

More polar isomer NMR CDCl$_3$ δ 7.3–7.1 (m, 10H); 6.3 (d, 1H); 5.3 (br, 1H); 4.7 (d, 1H); 4.6 (d, 1H); 4.1 (d, 1H); 3.9 (br, 1H); 3.7 (m, 1H); 2.65 (m, 3H); 2.5 (d, 3H); 2.1 (s, 3H); 1.9–1.7 (m, 2H); 0.9 (s, 9H).

Example 2

Compounds of the formula (I) wherein R$^1$ is ethyl (and other values are as in Example 1) were prepared in the same manner as in Example 1, except that propionyl chloride was used in place of acetyl chloride in step A. As in Example 1, the less polar and the more polar isomers were obtained.

Less Polar isomer DMSOd$_6$ δ 8.0 (d, 1H); 7.7 (d, 1H); 7.23 (m, 2H); 7.15 (m, 3H); 4.2 (d, 1H); 3.8 (m, 1H); 3.4 (m, 1H); 2.8 (br, 1H); 2.58 (d, 3H); 2.4 (m, 2H); 2.3 (m, 2H); 1.6 (m, 2H); 0.9 (m, 12H).

More Polar isomer DMSOd$_6$ δ 7.9 (d, 1H); 7.8 (d, 1H); 7.25–7.15 (m, 5H); 4.2 (d, 1H); 3.6 (m, 2H); 2.9 (br, 1H); 2.6 (d, 3H); 2.4 (m, 2H); 2.3 (m, 2H); 1.6 (m, 2H); 0.9 (m, 12H).

Example 3

Compounds of the formula (I) wherein R$^1$ is isopropyl (and other values are as in Example 1) were prepared in the same manner as in Example 1, except that isobutyryl chloride was used in place of acetyl chloride in step A. As in Example 1, the less polar and the more polar isomers were obtained.

Less Polar isomer DMSOd$_6$ δ 8.0 (d, 1H): 7.65 (d, 1H); 7.3–7.1 (m, 5H); 4.2 (d, 1H): 3.8 (m, 1H); 3.4 (dd, 1H); 2.8 (m, 2H); 2.6 (s, 3H): 2.4 (m, 2H); 1.8–1.6 (m, 2H); 0.95 (d, 6H); 0.9 (s, 9H).

More Polar isomer DMSOd$_6$ δ 7.9 (d, 1H); 7.8 (d, 1H); 7.3–7.1 (m, 5H); 4.2 (d, 1H); 3.7 (m, 1H), 3.5 (m, 1H); 2.9 (m, 2H); 2.6 (s, 3H); 2.4 (m, 2H); 1.7–1.5 (m, 2H); 0.98 (m, 15H).

Example 4

Compounds of the formula (I) wherein R$^1$ is phenyl (and other values are as in Example 1) were prepared in the same manner as in Example 1, except that benzoyl chloride was used in place of acetyl chloride in step A As in Example 1, the less polar and the more polar isomers were obtained.

Less Polar isomer DMSOd$_6$ δ 8.1 (d, 1H); 7.8.(d, 1H); 7.6 (m, 2H); 7.5 (m, 3H); 7.3 (m, 2H); 7.15 (m, 3H); 4.36 (d, 1H); 4.0 (m, 1H); 3.6 (m, 1H); 3.0 (br 1H); 2.6 (d, 3H); 2.4 (m, 2H); 1.8 (m, 2H); 0.95 (s, 9H).

More Polar isomer DMSOd$_6$ δ 8.0 (m, 2H); 7.6 (m, 2H); 7.4 (m, 3H); 7.3 (m, 3H); 7.15 (m, 3H); 4.3 (m, 1H); 3.6 (m, 1H); 3.2 (m, 1H): 3.0 (br, 1H); 2.5 (m, 5H); 1.7 (m, 2H); 0.95 (s, 9H).

Example 5

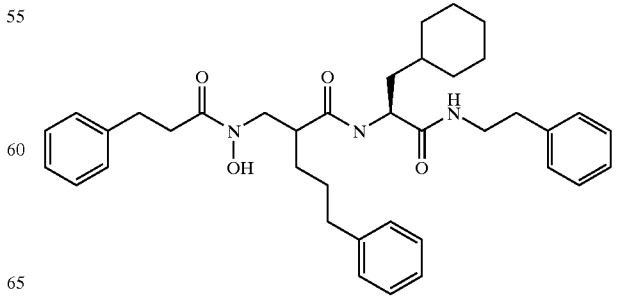

These compounds (isomers at the —CR⁴R⁵— position) were prepared as described in Example 1 but methyl 4-phenylbutenoate was replaced by methyl 5-phenylvalerate[4] and in step B, acetyl chloride was replaced by 3-phenylpropionyl chloride. In step D, S-tertbutyl-leucine N-methyl amide was replaced by S-β-cyclohexylalanine N-(2-phenylethyl)amide[7]. As in Example 1, the less polar and the more polar isomers were obtained. The NMR spectrum of these compounds was broad but both compounds have a mass spectrum MS (ES) (M+H): 612.

Less Polar isomer DMSOd₆ δ 7.4–7.0 (m, 15H); 4.3 (m, 1H); 3.8–3.5 (m, 2H); 3.3 (q, 2H); 3.0–2.6 (m 10H); 1.7–0.8 (m, 17H).

More polar isomer DMSOd₆ δ 7.4–7.0 (m, 15H); 4.3 (m, 1H); 3.6 (m, 1H); 3.4–3.1 (m, 2H); 3.3 (q, 2H); 3.0–2.6 (m, 12H); 1.7–0.8 (m, 15H).

Example 6

Compounds of the formula (I) wherein $R^1$ is methyl, $R^4$ is 4-fluorophenylbutyl (and other values are as in Example 5) were prepared in the same manner as in Example 1, but methyl 4-phenylbutenoate was replaced by methyl 5-(4-fluorophenyl)hexanoate which was prepared as follows. In step D the S-tertbutyl-leucine N methyl amide was replaced by S-β-cyclohexylalanine N-(2-phenylethyl)amide.

Less Polar isomer DMSOd₆ δ 7.4–7.0 (m, 9H); 4.3 (m, 1H); 3.8–3.7 (m, 1H); 3.6–3.5 (m, 1H); 3.35. (m, 2H); 2.8–2.6 (m, 3H); 2.0 (s, 3H); 1.7–0.8 (m, 21H).

More Polar isomer DMSO₆ δ 7.4–7.0 (m, 9H); 4.3 (m, 1H), 3.8–3.6 (m, 2H); 3.6–3.5 (m, 2H); 2.8–2.5 (m, 4H); 2.0 (s, 3H); 1.7–0.8 (m, 20H).

5-(4-Fluorophenyl)-hexanoic acid[6] (3.0 g, 0.015M) was dissolved in methanol (30 ml), conc. sulphuric acid (10 drops) was added and reaction mixture stirred under reflux for 16 hours. After concentrating in vacuo, dichloromethane (30 ml) was added, the mixture was washed with saturated sodium bicarbonate solution (2×20 ml), dried and the filtrate was concentrated in vacuo to give methyl 5-(4-fluorophenyl) hexanoate as an orange oil (3.11 g, 97% yield): NMR (CDCl₃) 1.35 (m, 2H), 1.61 (m, 4H), 2.30 (t, 2H), 2.58 (t, 2H), 3.65 (s, 3H), 6.95 (dd, 2H), 7.12 (dd, 2H).

Example 7

Typical tablet formulations for a compound of this invention or a pharmaceutically-acceptable salt thereof ('Compound X') are:

|  | mg/tablet |
|---|---|
| (a) Tablet Formulation 1 | |
| Compound X | 100 |
| Lactose Ph.Eur | 179 |
| Croscarmellose sodium | 12 |
| Polyvinylpyrrolidone | 6 |
| Magnesium stearate | 3 |
| (b) Tablet Formulation II | |
| Compound X | 250 |
| Lactose Ph.Eur | 215 |
| Croscarmellose sodium | 20 |
| Polyvinylpyrrolidone | 10 |
| Magnesium stearate | 5 |

The tablets may be prepared by conventional procedures well known in the pharmaceutical art and may be film coated with typical coating materials such as hydroxypropylmethylcelluose.

REFERENCES

1. Deshmukh, A. R. et al J. Org. Chem. (1992) 57(2) 667–70
2. Hart, David J. et al. J. Am. Chem. Soc. (1998) 110(5) 1631–3
3. Kumar, Punit. Org . Prep. Proceed. Int. (1997) 29(4) 477–80
4. Inomata, Katsuhiko. et al. Chem. Lett. (1990) 9, 1567–70
5. Rosenblum, Stuart B. et al J. Med. Chem. (1998) 41(6) 973–80
6. Gapinski, D. Mark; et al J. Med. Chem. (1990), 33(10), 2807–13.
7. PCT Application Publication No. WO 9314056.

What is claimed is:

1. A compound of the formula (I):

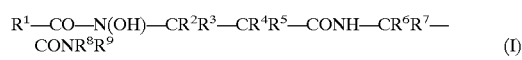

wherein:

$R^1$ is $C_{1-6}$alkyl, aryl or aryl$C_{1-6}$alkyl;

$R^2$ is hydrogen, $C_{1-6}$alkyl, $C_{3-8}$cycloalkyl, aryl or aryl$C_{1-6}$alkyl;

$R^3$ is hydrogen, $C_{1-6}$alkyl or aryl$C_{1-6}$alkyl;

or $R^2$ and $R^3$, together with the carbon atom to which they are joined, form a $C_{3-8}$cycloalkyl ring;

$R^4$ is benzyl, phenethyl, phenylpropyl, phenylbutyl or fluorophenylbutyl;

$R^5$ is hydrogen, $C_{1-6}$alkyl or aryl$C_{1-6}$alkyl;

$R^6$ is isobutyl, tertbutyl, 1,1-dimethylmethylthiomethyl, cyclopentylmethyl, cyclohexylmethyl or benzyl;

$R^7$ is hydrogen or $C_{1-6}$alkyl;

$R^8$ is hydrogen, $C_{1-6}$alkyl, $C_{3-8}$cycloalkyl, $C_{3-8}$cycloalkenyl, aryl$C_{1-6}$alkyl, heteroaryl$C_{1-6}$alkyl or heterocyclyl$C_{1-6}$alkyl;

$R^9$ is hydrogen or $C_{1-6}$alkyl;

or $R^8$ and $R^9$, together with the nitrogen atom to which they are joined, form a heterocyclic ring;

wherein any group or ring in $R^1$–$R^9$ is optionally substituted;

or a pharmaceutically-acceptable salt or in vivo hydrolysable precursor thereof.

2. A compound as claimed in claim 1 wherein $R^1$ is selected from $C_{1-6}$alkyl; $C_{1-6}$alkyl interrupted by an oxygen or sulphur atom; phenyl$C_{1-6}$alkyl; phenyl$C_{1-6}$alkyl interrupted by oxygen or sulphur; and aryl.

3. A compound as claimed in claim 1 of the formula (II):

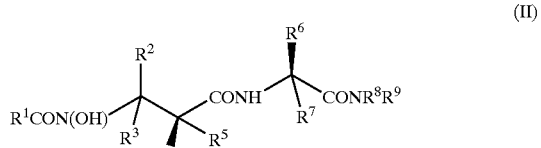

wherein $R^1$–$R^9$ are as defined in claim 1.

4. A pharmaceutical composition which comprises a compound of the formula (I) or a pharmaceutically acceptable salt or an in vivo hydrolysable precursor and pharmaceutically acceptable carrier.

5. A pharmaceutical composition which comprises a compound of the formula (II) or a pharmaceutically acceptable salt or an in vivo hydrolysable precursor and pharmaceutically acceptable carrier.

6. A compound of the formula (I) or (II) or a pharmaceutically acceptable salt or in vivo hydrolysable precursor thereof for use in a method of therapeutic treatment of the human or animal body.

7. A method of treating a disease condition mediated by one or more metalloproteinase enzymes which comprises administering to a warm-blooded animal an effective amount of a compound of the formula (I) or (II) or a pharmaceutically acceptable salt or in vivo hydrolysable precursor thereof.

* * * * *